United States Patent [19]

Micetich

[11] 4,171,304

[45] Oct. 16, 1979

[54] 2-IODOMETHYLPENAMS

[75] Inventor: Ronald G. Micetich, Edmonton, Canada

[73] Assignee: Connlab Holdings Limited, St. Laurent, Canada

[21] Appl. No.: 855,978

[22] Filed: Nov. 30, 1977

Related U.S. Application Data

[62] Division of Ser. No. 802,137, May 31, 1977, abandoned.

[30] Foreign Application Priority Data

Jun. 14, 1976 [GB] United Kingdom ............... 24499/76

[51] Int. Cl.$^2$ ............................................. C07D 499/04
[52] U.S. Cl. .................................................. 260/239.1
[58] Field of Search ...................................... 260/239.1

[56] References Cited

U.S. PATENT DOCUMENTS

| 3,954,732 | 5/1976 | Kamiya et al. ............... 260/239.1 |
| 4,009,159 | 2/1977 | Kamiya et al. ............... 260/239.1 |

OTHER PUBLICATIONS

Micetich et al., Tetrahedron Letters No. 13, pp. 979–982 (3/1976).
Kamiya et al., Tetrahedron Letters, p. 3001 (1973).
Kamiya et al., Chemical Abstr., vol. 80, 82953(b) (1974).
Kamiya et al., Chemical Abstr., vol. 81, 25687(q) (1974).

*Primary Examiner*—Gerald A. Schwartz
*Attorney, Agent, or Firm*—Cushman, Darby & Cushman

[57] ABSTRACT

Novel 2-iodomethyl-penicillanic acid derivatives are prepared and are useful for the preparation of bioactive 2,3-methylenepenams and 2-methylceph-3-ems.

7 Claims, No Drawings

2-IODOMETHYLPENAMS

This is a division, of application Ser. No. 802,137 filed May 31, 1977, now abandoned.

The present invention relates to novel 2-iodomethylpenicillanic acid derivatives and to a process for preparing same.

PRIOR ART

Known commercial cephalosporins such as cephalexin, cephaloglycin, cephaloridine, cephalothin, cefazolin, and cephapirin are obtained by a number of different processes, which also involve preparing a variety of intermediates for the respective cephalosporins.

Cephalosporin C and desacetoxycephalosporin C can be obtained by fermentation processes. The aminoadipyl moiety in these compounds is removed by various chemical processes to give 7-aminocephalosporanic acid (7-ACA) and 7-aminodesacetoxycephalosporanic acid (7-ACDA) respectively. These basic compounds are then reacylated to introduce the appropriate group. In most instances, further chemical modification of the molecule is necessary to provide the desired antibiotic. The disadvantage of this route is the relative difficulty and consequent high cost of preparing and isolating cephalosporin C and desacetoxycephalosporin C. As a reslt, alternate methods have been investigated.

Another approach makes use of the readily available, low cost, commercial penicillins G and V as starting materials. Cephalexin, a commercially important cephalosporin, is manufactured by a multi-stage process starting from penicillin V, the process employed being illustrative of this method. Penicillin V is converted to its sulfoxide which is rearranged under appropriate conditions to the cephalosporin. The cephalosporin is then deacylated to 7-ADCA or its ester, and reacylated by a variety of described processes to cephalexin. The necessity to protect and later deprotect the amine and/or acid functions during some of these operations adds to the number of stages and hence to the cost of this process.

A useful alternate approach is to react the penicillin sulfoxide with a mercaptan when an azetidinone disulfide is obtained. Analogous sulfuramides are obtained by heating the sulfoxide in the presence of a silylated amide, or by treating the unsym-azetidinone disulfide with a suitable amine. These compounds on chlorination or bromination by various reagents produce the 2-chloro- (or bromo-) methylpenams or the 3-chloro- (or bromo-) cephams, depending on the reaction conditions used. The 2-chloro- (or bromo-) methylpenams are readily converted on standing at room temperature (in the solid state or in solution) or quicker on heating to the more stable 3-chloro- (or bromo-) cephams. These latter compounds can be dehydrohalogenated to the respective cephems, and these in turn deacylated by known processes to 7-ADCA and its derivatives, which are starting materials for certain commercial cephalosporins.

The 2-chloro (or bromo-) methylpenicillins are useful synthetic intermediates. The chloro- or bromo- groups have been replaced by other functionalities to provide 2-substituted-methylpenicillins and 3-substitutedcephalosporins which are biologically active. In addition the 2-bromomethylpenicillin has been converted to the 2,3-methylenepenicillins and the 2-methylceph-3-ems which are also biologically active compounds. In the latter case the compounds are reported to be more active than the analogous 3-methylceph-3-ems.

Since the iodo group is a good leaving group, the 2-iodomethylpenicillins are better synthetic intermediates than the 2-chloro- (or bromo-) methylpenicillins.

THE INVENTION

In accordance with the present invention, there is now provided the novel compounds, the 2-iodomethylpenams, 1 (Flowsheet 1) which have been derived from the thiazineazetidinones, 2, the 1,2,4-dithiaz-3-eneazetidinones, 3, the sym-azetidinone disulfides, 4, and the unsym-azetidinone disulfides, 5, by a novel process.

The novel compounds of the present invention are the 2-iodomethylpenams, 1, corresponding to the general formula:

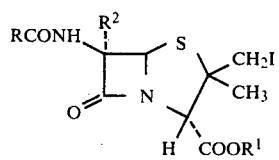

wherein the RCO group is an amino protecting group, $R^1$ is hydrogen or a carboxy protecting group and $R^2$ is hydrogen or methoxy.

Essentially, the RCO group is any of the amino protecting groups well known in the penicillin and cephalosporin antibiotic literature. The RCO group can be any of the amino protecting groups used to protect an amino group in peptide synthesis chemistry and particularly an acyl group. More particularly R can stand for $C_{1-4}$ alkyl, cyanomethyl, thienylmethyl, furylmethyl, tetrazolylmethyl, phenylmethyl, phenoxymethyl, phenoxyisopropyl, $R^3O—$, $R^3S—$ or $R^3R^4N—$ wherein $R^3$ is lower alkyl, phenyl, phenylloweralkyl or trichloroethyl, $R^4$ is hydrogen or is the same as $R^3$; α-hydroxybenzyl, α-aminobenzyl or benzyl-α-carboxylic acid wherein the α-hydroxy, α-amino or α-carboxylic acid moieties may be optionally protected by an easily removable group. Numerous other compounds which form amino protecting groups which can be used in the R position are known in the prior art such as those disclosed in U.S. Pat. Nos. 2,479,295, 2,479,296, 2,479,297, 2,562,407 to 2,562,411 and 2,623,876.

The $R^1$ group may be hydrogen or a carboxy protecting group. As an example of a carboxy protecting group there may be mentioned the lower alkyl, 2,2,2-trichloroethyl, benzyl, p-nitrophenyl, p-methoxybenzyl, benzhydryl, fluorenyl, phenacyl, methoxymethyl, phenoxymethyl, benzyloxymethyl or trimethylsilyl.

These compounds are also useful in preparing known cephalosporins and are also useful intermediates for the preparation of the bioactive 2,3-methylenepenams and 2-methylceph-3-ems.

The 2-iodomethylpenams, 1, readily convert to the 3-iodocephams, 6, on standing at room temperature even in the solid state. The pmr spectra of the 2-iodomethylpenams, 1, are different from those of the 3-iodocephams, 6, and can be used to distinguish between them.

Generally, the novel 2-iodomethylpenams, 1, of the present invention are prepared by iodinating either the dithiazineazetidinones, 3, the thiazineazetidinones, 2, the sym-azetidinone disulfides, 4, or the unsym-azetidinone disulfides, 5, in a suitable solvent with an iodinating agent, preferably iodine, preferably in the presence of moisture. These reactions are schematically illustrated in Flowsheet 1.

In Flowsheet 1, the values of R, $R^1$ and $R^2$ are as defined previously and $R^5$ stands for lower alkyl,-$(CH_2)_nCOO$-lower alkyl where n is an interger from 1 to 3, phenyl, heteroaryl, benzyl and the group

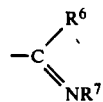

where $R^6$ stands for lower alkyl, phenyl, heteroaryl, -O-loweralkyl, -O-phenyl, -S-lower alkyl, -S-phenyl, or $NHR^8$, and $R^7$ and $R^8$ may be the same or different and each taken from the group H, lower alkyl, phenyl or heteroaryl.

The conditions of the iodination reaction (time and temperature of the reaction, stoichiometry, concentration and presence of impurities) are important in determining the nature of the products. Short reaction times (5 minutes to 6 hrs) and low temperatures (0° to 25° C.) favour the formation of the 2-iodomethylpenams, 1, which are the primary products formed by kinetic control. Longer reaction times and higher temperatures favour the formation of the 3-iodocephams, 6, which are the thermodynamically more stable compounds and are in fact formed from the 2-iodomethylpenams, 1. Impurities such as air or oxygen or metal salts such as ferric chloride catalyse the iodination reaction. In the absence of moisture and in presence of nitrogen, the iodination of the thiazineazetidinone, 2, the dithiazineazetidinone, 3, and the symazetidinone disulfide 4, proceeds very slowly or not at all.

As iodinating agent there may be used iodine, an iodinating agent such as N-iodosuccinimide or sulfenyl iodides, or mixtures thereof. The reagent of choice is iodine.

As suitable solvents, there may be used dioxane, tetrahydrofuran, ethylacetate, methylene chloride, toluene and similar solvents.

The methods of preparation of the dithiazineazetidinones, 3, and the thiazineazetidinones, 2, is summarised in Flowsheet 2. The dithiazineazetidinones, 3, are made from the 6-thioamides of penicillin sulfoxides, 8, and their preparation is described in Can. Appl. Ser. No. 208,248, filed Aug. 30, 1974. The thiazineazetidinones, 2, are described in U.S. Pat. No. 3,594,389, July 10, 1971, while the sym-azetidinone disulfides, 4, are obtained from azetidinone disulfides [Tetra. Letters, 3001 (1975)] or compounds 2 or 3 [Tetra Letters, 979 (1976)].

The unsym-azetidinone disulfides, 5, are obtained by heating a penicillin sulfoxide (either the α- or β-sulfoxides or a mixture thereof) of formula 7, with a mercaptan [Tetra. Letters, 3001 (1973)] or with a thioamide of the formula $R^6CSNHR^7$, where $R^6$ and $R^7$ are as previously defined. The reaction is carried out in the presence of a suitable solvent such as for example dioxane or toluene. As an example of suitable thioamides, there may be mentioned thioacetamide, thiourea, thiosemicarbazide, thiocarbamates and dithiocarbamates.

In the case of the dithiazineazetidinones, 3, it is not necessary to isolate the compounds 3, so that a simplification of the process is possible, starting from the penicillin sulfoxide thioamide.

The 2-iodomethylpenams, 1, on storage at room temperature as a solid or in solution, or better on warming in a suitable solvent is converted to the 3-iodocepham, 6. These compounds, 6, on solution in pyridine are converted in quantitative yield to the desacetoxycephalosporins. These compounds are precursors of commercially important cephalosporins such as cephalexin.

FLOWSHEET 1

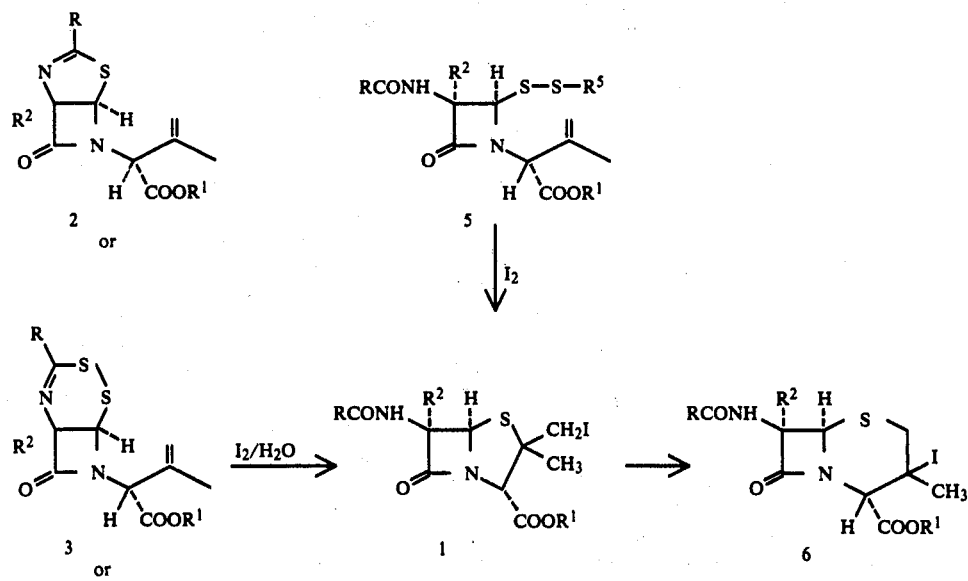

-continued
FLOWSHEET 1

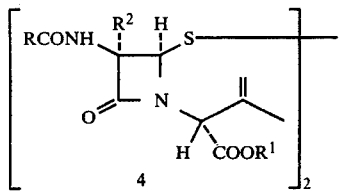

FLOWSHEET 2

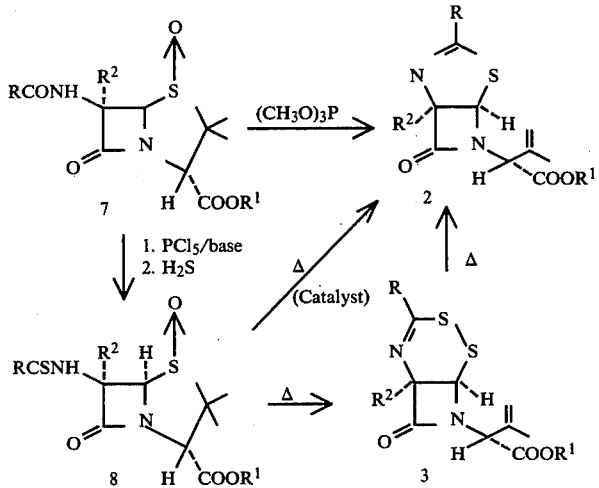

The 2-iodomethylpenams, 1, are oxidised by agents such as peracetic acid or m-chloroperbenzoic acid to the 2-iodomethylpenam sulfoxides, 10 (see Flowsheet 3). Both these compounds when treated separately with a suitable base, such as 1,5-diazabicyclo[5.4.0]undec-5-ene (DBU), or 1,5-diazabicyclo[4.3.0]non-5-ene (DBN), or 1,4-diazabicyclo[2.2.2]octane (Dabco), or 1,8-bis-(dimethylamino)-naphthalene (Proton Sponge), or lithium diisopropylamide or N-methyldiisopropylamine (Hunigs Base), are converted to the 2,3-methylenepenams, 9, and the 2,3-methylenepenam sulfoxides, 11, respectively. Compound 11 is deoxygenated by PCl₃ in DMF to 9 [J. Amer. Chem. Soc., 97, 5020 (1975)]. The 2,3-methylenepenams, 9, have useful antibiotic activity (Ger. Offen. 2,354,178, May 30, 1974). On treatment with Lewis acids, such as aluminium trichloride, aluminium tribromide or titanium tetrachloride they are converted to the 2-methylceph-3-ems, 12, compounds with excellent antibacterial activity [Ger. Offen. 2,412,513, Sept. 26, 1974; J. Amer. Chem. Soc., 98, (1976)].

FLOWSHEET 3

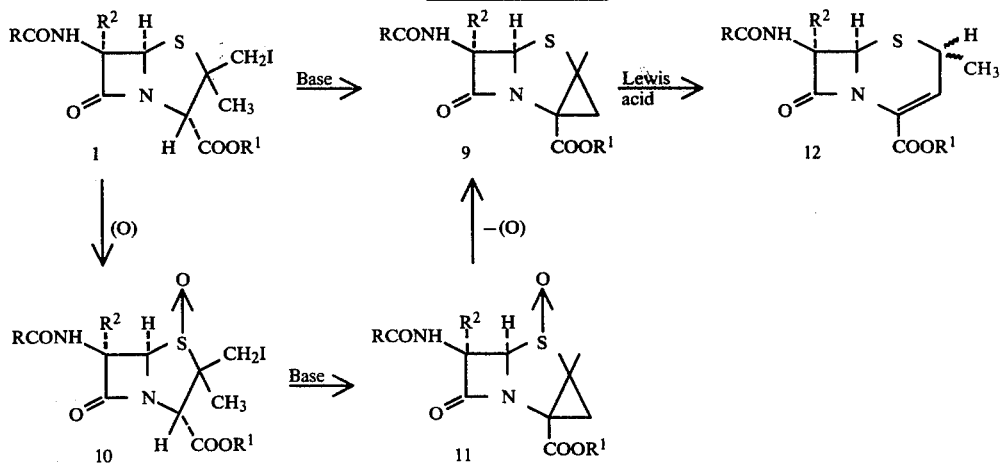

EXAMPLES

The present invention will be more readily understood by referring to the following examples which are given only to illustrate the invention rather than limit its scope.

EXAMPLE 1

Benzhydryl 7-Phenoxymethylthioamidopenicillinate Sulfoxide, 8, (R=$\phi$OCH$_2$, R$^1$=CH$\phi_2$, R$^2$=H).

Benzhydryl 7-phenoxyacetamidopenicillinate sulfoxide [J. Chem. Soc., 2019 (1975)]; 26.6 g., (50 mmoles) was dissolved in methylene chloride (375 ml) and the resulting solution cooled to −30° C. To the stirred cooled solution, dimethylaniline (24.2 g., 200 mmole) and well powdered phosphorus pentachloride (20.8 g., 100 mmoles) were added one after the other. On the addition of the PCl$_5$ there was a mildly exothermic reaction, the temperature reaching −22° C. before cooling again to −30° C. All the solid dissolved in about 15 mins, and the color of the solution changed from brown to dark green. After a reaction time of 30 mins, the reaction mixture was cooled to −50° C. and hydrogen sulfide bubbled through the solution for 20 mins, maintaining the temperature of the reaction mixture below −40° C. The color of the solution changed from dark green to yellow. After a further 1 hr at −40° C., the reaction mixture was poured with stirring into cold aqueous saturated sodium bicarbonate (750 ml). The separated organic layer was then washed in sequence with water, then cold normal hydrochloric acid, then with water, and finally dried over MgSO$_4$. Filtration and concentration of the organic layer gave 31.7 g. (theoretical 27.4 g.) of the crude benzhydryl 7-phenoxyacetamidopenicillinate sulfoxide as a yellow-green foam. The nmr spectrum (CDCl$_3$) of the crude product showed that it was the thioamide contaminated with dimethylaniline or its salt.

A partial purification was effected (recovery 0.85 g. from 1 g. of crude) by dissolving the crude material (1 g.) in methylene chloride (10 ml), adding pyridine (0.5 ml) followed by ether (25 ml). The resulting mixture was cooled to −70° C. and hexane (75 ml) slowly added, when the desired purified thioamide separated as a white powder. The thioamide was separated by filtration, washed with hexane, and dried to give a white powder (0.85 g.) m.p. 125°-129° C., whose nmr spectrum showed it was free of dimethylaniline or its salts.

Pure benzhydryl 7-phenoxyacetamidopenicillinate sulfoxide was obtained (in about 70% yield) by chromatographing the crude material on silica (Malinkrodt Silicar CC7) using methylene chloride-ether gradient elution. This material could be recrystallised from ethanol (the crude material undergoes β-lactam cleavage), to give a white solid, m.p. 133°-134° C. The nmr (CDCl$_3$) spectrum: δ0.9 and 1.75 (ss, 6H, gem.-C$\underline{H}_3$), 4.93 (s, 1H, C$_3$—$\underline{H}$), 5.05 (s, 2H, —OC$\underline{H}_2$—), 5.20 (d, 1H, C$_5$—$\underline{H}$), 6.77 to 7.75 (m, 17H, C$_6$—$\underline{H}$, aryl and C$\underline{H}\phi_2$), 10.08 (d, 1H, N$\underline{H}$), is in agreement with the structure.

In a similar manner, starting with methyl 7-phenoxyacetamidopenicillinate sulfoxide, p-nitrophenyl 7-phenoxyacetamidopenicillinate sulfoxide, 2,2,2-trichloroethyl 7-phenoxyacetamidopenicillinate sulfoxide, benzhydryl 7-phenylacetamidopenicillinate sulfoxide, methyl 7-phenylacetamidopenicillinate sulfoxide, and benzhydryl 7-benzamidopenicillinate sulfoxide the following compounds were made: methyl 7-phenoxymethylthioamidopenicillinate sulfoxide, p-nitrobenzyl 7-phenoxymethylthioamidopenicillinate sulfoxide, 2,2,2-trichloroethyl 7-phenoxymethylthioamidopenicillinate sulfoxide, benzhydryl 7-phenylmethylthioamidopenicillinate sulfoxide, methyl 7-phenylmethylthioamidopenicillinate sulfoxide, and benzhydryl 7-phenylthioamidopenicillinate sulfoxide.

EXAMPLE 2

Benzhydryl 3-Phenoxymethyl-4,5-Dithia-2,7-Diazabicyclo[4.2.0]Oct-2-Ene-8-One-7-Isopropenyl Acetate 3, (R=$\phi$OCH$_2$, R$^1$=CH$\phi_2$, R$^2$=H)

A solution of freshly prepared pure benzhydryl 6-phenoxymethylthioamidopenicillinate sulfoxide (500 mg.) in toluene (125 ml) was heated for 2 hrs (in an oil bath at 135° C.) with stirring under reflux, under nitrogen, in a flask fitted with a Dean-Stark trap. The toluene was removed in vaccuo. An nmr spectrum (CDCl$_3$) of the waxy residue showed complete reaction with formation of benzhydryl 3-phenoxymethyl-4,5-dithia-2,7-diazabicyclo[4.2.0]oct-2-ene-8-one-7-isopropenylacetate, δ1.80

(s, 3H, —C(=CH$_2$)—CH$_3$), 4.73 to 5.08

(m, 5H, CHCOOCH$\phi_2$, —OCH$_2$, and —C(CH$_3$)=CH$_2$), 5.66 (m, 2H, β-lactam $\underline{H}$), 6.86 to 7.49 (m, 16H, aryl H and C$\underline{H}\phi_2$). The compound is unstable and was used as soon as it was prepared.

In a similar manner, using methyl 7-phenoxymethylthioamidopenicillinate sulfoxide the methyl 3-phenoxymethyl-4,5-dithia-2,7-diazabicyclo[4.2.0]oct-2-ene-8-one-7-isopropenyl acetate was prepared.

EXAMPLE 3

Benzhydryl 3-Phenoxymethyl-4-Thia-2,6-Diazabicyclo[3.2.0]Hept-2-Ene-7-One-6-Isopropenylacetate, 2, (R=$\phi$OCH$_2$, R$^1$=CH$\phi_2$, R$^2$=H), from Benzhydryl 6-Phenoxyacetamidopenicillinate Sulfoxide, 7, (R=$\phi$OCH$_2$, R$^1$=CH$\phi_2$ R$^2$=H)

A mixture of benzhydryl 6-Phenoxyacetamidopenicillinate sulfoxide (5 g., 1 mmole) and trimethyl phosphite (0.25 g., 2 mmole) in toluene (40 ml) was heated under reflux for 2.5 hrs, by which time a thin layer chromatogram indicated complete reaction. The reaction mixture was washed well with water (6 times), and the toluene layer concentrated in vaccuo.

The resulting gum was dissolved in the minimum amount of ether and the solution cooled at −10° C. overnight. The white crystalline powder was filtered and dried and weighed 3.4 g., m.p. 83°-85° C. The nmr (CDCl$_3$) spectrum δ1.72

(s, 3H, —C(=CH$_2$)—CH$_3$), 4.8 to 5.05

(m, 5H, OCH₂, CHCOOCH$\phi_2$ —< CH₃ / CH₂ ), 5.95 (m, 2H, β-lactam H's), 6.85 to 7.4 (m, 16H, aryl H's, CH$\phi_2$) is characteristic of this compound.

In a similar way, starting with methyl 6-phenoxyacetamidopenicillinate sulfoxide, trichlororethyl 6-phenoxyacetamidopenicillinate sulfoxide, p-nitrobenzyl 6-phenoxyacetamidopenicillinate sulfoxide, benzhydryl 6-phenylacetamidopenicillinate sulfoxide, and methyl 6-phenylacetamidopenicillinate sulfoxide the following compounds were made: methyl 3-phenoxymethyl-4-thia-2,6-diazabicyclo[3.2.0]hept-2-ene-7-one-6-isopropenyl acetate, trichloroethyl 3-phenoxymethyl-4-thia-2,6-diazabicyclo[3.2.0]hept-2-ene-7one-6-isopropenyl acetate, p-nitrobenzyl 3-phenoxymethyl-4-thia-2,6-diazabicyclo[3.2.0]hept-2-ene-7-one-6-isopropenyl acetate, benzhydryl 3-phenylmethyl-4-thia-2,6-diazabicyclo [3.2.0]hept-2-ene-7-one-6-isopropenyl acetate, and methyl 3-phenylmethyl-4-thia-2,6-diazabicyclo[3.2.0]hept-2-ene-7-one-6-isopropenyl acetate.

EXAMPLE 4

Benzhydryl 3-Phenoxymethyl-4-Thia-2,6-Diazabicyclo[3.2.0]Hept-2-Ene-7-One-6-Isopropenyl acetate, 2, (R=$\phi$OCH₂, R¹=CH$\phi_2$, R²=H) from Benzhydryl 6-Phenoxymethylthioamidopenicillinate Sulfoxide, 8, (R=$\phi$OCH₂, R¹=CH$\phi_2$, R²=H).

A solution of benzhydryl 6-phenoxymethylthioamidopenicillinate sulfoxide (500 mg.) in toluene (125 ml) was heated under reflux overnight (16 hrs) in an oil bath maintained at 120° C. The reaction mixture was taken to dryness to give a thick wax whose nmr (CDCl₃) spectrum was characteristic of benzhydryl 3-phenoxymethyl-4-thia-2,6-diazabicyclo[3.2.0]hept-2-ene-7-one-6-isopropenyl acetate (as in example 3).

In a similar way starting with methyl 7-phenoxymethylthioamidopenicillinate sulfoxide, p-nitrobenzyl 7-phenoxymethylthioamidopenicillinate sulfoxide, 2,2,2-trichloroethyl 7-phenoxymethylthioamidopenicillinate sulfoxide, methyl 7-phenylmethylthioamidopenicillinate sulfoxide, and benzhydryl 7-phenylthioamidopenicillinate sulfoxide, the following compounds were made: methyl 3-phenoxymethyl-4-thia-2,6-diazabicyclo[3.2.0]hept-2-ene-7-one-6-isopropenylacetate, p-nitrophenyl 3-phenoxymethyl-4-thia-2,6-diazabicyclo[3.2.0]hept-2-ene-7-one-6-isopropenylacetate, 2,2,2-trichloroethyl 3-phenoxymethyl-4-thia-2,6-diazabicyclo[3.2.0]hept-2-ene-7-one-6-isopropenylacetate, methyl 3-phenylmethyl-4-thia-2,6-diazabicyclo[3.2.0]hept-2-ene-7-one-6-isopropenylacetate, and benzhydryl 3-phenyl-4-thia-2,6-diazabicyclco[3.2.0]hept-2-ene-7-one-6-isopropenylacetate.

EXAMPLE 5

Sym-(Methyl-3-Phenoxyacetamidoazetidinone-1-Isopropenyl Acetate)-4-Disulfide, 4, (R=$\phi$OCH₂, R¹=CH₃, R²=H) from Methyl 3-Phenoxymethyl-4,5-Dithia-2,7-Diazabicyclo[4.2.0]Oct-2-Ene-8-One-7-Isopropenylacetate, 3 (R=$\phi$OCH₂, R¹=CH₃, R²=H)

Methyl 6-phenoxymethylthioamidopenicillinate sulfoxide (1.0 g., 2.6 mmoles) was converted to methyl 3-phenoxymethyl-4,5-dithia-2,7-diazabicyclo[4.2.0]oct-2-ene-8-one-7-isopropenylacetate, 3, by the method described in example 2. The total residue from the thermolysis in toluene was dissolved in purified dioxane (500 mls), iodine (330 mg., 1.3 mmole) added and moist air bubbled through the stirred solution at ambient temperature for 20 hrs. The solution was concentrated, the residue dissolved in methylene chloride and the resulting solution washed with aqueous sodium thiosulfate (twice) and water (twice), dried over magnesium sulfate and charcoal, and concentrated. The resulting yellow foam weighed 0.9 g., (94%) and was the sym-azetidinonedisulfide, 4 (R=$\phi$OCH₂, R¹=CH₃, R²=H). The nmr (CDCl₃) spectrum δ1.91

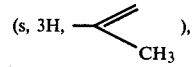
(s, 3H, —< CH₃ ), 3.75 (s, 3H, COOCH₃), 4.6 (s, 2H, —OCH₂), 4.9 (s, 1H, CHCOOCH₃), 5.1 and 5.22

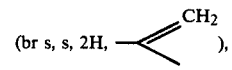
(br s, s, 2H, —< CH₂ ), 5.37 to 5.52 (m, 2H, β-lactam H's), 6.95 to 7.5 (m, 5H, C₆H₅), 7.8 (d, 1H, NH), is consistent with the assigned structure.

EXAMPLE 6

Sym-(Methyl 3-Phenoxyacetamidoazetidinone-1-Isopropenyl Acetate)-4-Disulfide, 4 (R=$\phi$OCH₂, R¹=CH₃, R²=H) from Methyl 3-Phenoxymethyl-4-Thia-2,6-Diazabicyclo[3.2.0]Hept-2-Ene-7-One-6-Isopropenylacetate, 2 (R=$\phi$OCH₂, R¹=CH₃, R²=H).

When methyl 3-phenoxymethyl-4-thia-2,6-diazabicyclo[3.2.0]hept-2-ene-7-one-6-isopropenylacetate, 2 (R=$\phi$OCH₂, R¹=CH₃, R²=H) (100 mg., 0.29 mmoles) was treated with an atomic equivalent (40 mg., 0.15 mmoles) of iodine in dioxane (100 mls) in the same was as described in Example 5, the same product 4, was obtained. The nmr spectrum was identical to that of the product in Example 5.

EXAMPLE 7

Benzhydryl 6-Phenoxyacetamido-2-Iodomethyl-2-Methylpenam-3-Carboxylate, 1, (R=$\phi$OCH₂, R¹=CH$\phi_2$, R²=H) from Benzhydryl 3-Phenoxymethyl-4-Thia-2,6-Diazabicyclo[3.2.0]Hept-2-Ene-7-One-6-Isopropenylacetate, 2, (R=$\phi$OCH₂, R¹=CH$\phi_2$, R²=H)

A mixture of benzhydryl 3-phenoxymethyl-4-thia-2,6-diazabicyclo[3.2.0]hept-2-ene-7-one-6-isopropenyl acetate, 2, (150 mg., 0.3 mmole) and iodine (127 mg., 0.5 mmols) in methylene cnloride (9 ml) was stirred at ambient temperature for 15 mins. Water (9 ml) was then added to the stirred solution and air bubbled through the solution. After a reaction time of 45 mins the reaction mixture was washed with aqueous sodium thiosulfate, then water, and the organic layer dried over magnesium sulfate. Filtration and concentration gave the product as a pale yellow foam. Analysis of the foam by nmr spectroscopy showed a mixture of the 2-methylpenam, 1 (R=φOCH₂, R¹=CHφ₂, R²=H, 69.4%), the starting material 2 (16.7%), and the 3-iodocepham, 6 (13.8%). The 2-iodomethylpenam could be isolated by thick layer chromatography. On standing (in solution or as a foam) at room temperature the 2-iodomethylpenam 1 is slowly converted to the thermodynamically more stable 3-iodocepham, 6. If the iodination reaction is allowed to run for longer periods of time, increasing amounts of 6 are obtained and after 10 hrs to a week, the major product is 6.

Nmr spectroscopy is a convenient method of distinguishing between 1 and 6. Thus the nmr (CDCl₃) spectrum of 1, δ1.42 (s, 3H, C₂—CH₃), 3.42 (s, 2H, CH₂I), 4.62 (s, 2H, OCH₂), 4.8 (s, 1H, CHCOOCHφ₂), 5.8 (m, 2H, β-lactam H's), 6.9 to 7.6 (m, 16H, aryl H and CHφ₂), is quite distinctive from 6 which is characterised by a singlet at δ2.0 for the C₃—CH₃ group and an AB type quartet centered at about δ2.8 for the C₂—CH₂ group.

In a similar manner starting from methyl 3-phenoxymethyl-4-thia-2,6-diazabicyclo[3.2.0]hept-2-ene-7-one-6-isopropenylacetate, trichloroethyl 3-phenoxymethyl-4-thia-2,6-diazabicyclo[3.2.0]hept-2-ene-7-one-6-isopropenylacetate, p-nitrobenzyl 3-phenoxymethyl-4-thia-2,6-diazabicyclo[3.2.0]hept-2-ene-7-one-6-isopropenylacetate, benzhydryl 3-phenylmethyl-4-thia-2,6-diazabicyclo[3.2.0]hept-2-ene-7-one-6-isopropenylacetate, and methyl 3-phenylmethyl-4-thia-2,6-diazabicyclo[3.2.0]hept-2-ene-7-one-6-isopropenylacetate, the following compounds can be made:
  methyl 6-phenoxyacetamido-2-iodomethyl-2-methylpenam-3-carboxylate, trichloroethyl 6-phenoxyacetamido-2-iodomethyl-2-methylpenam-3-carboxylate, p-nitrophenyl 6-phenoxyacetamido-2-iodomethyl-2-methylpenam-3-carboxylate, benzhydryl 6-phenylacetamido-2-iodomethyl-2-methylpenam-3-carboxylate, and methyl 6-phenylacetamido-2-iodomethyl-2-methylpenam-3-carboxylate.

EXAMPLE 8

Benzhydryl 6-Phenoxyacetamido-2-Iodomethyl-2-Methylpenam-3-Carboxylate, 1 (R=φOCH₂, R¹=CHφ₂, R²=H) from Benzhydryl 3-Phenoxymethyl-4,5-Dithia-2,7-Diazabicyclo[4.2.0]Oct-2-Ene-8-One-7-Isopropenyl Acetate, 3 (R=φOCH₂, R¹=CHφ₂, R²=H)

A freshly prepared solution of benzhydryl 3-phenoxymethyl-4,5-dithia-2,7-diazabicyclo[4.2.0]oct-2-ene-8-one-7-isopropenyl acetate in toluene, prepared as described in Example 2, was iodinated as described in Example 7 and gave essentially the same results.

EXAMPLE 9

Methyl 6-Phenoxyacetamido-2-Iodomethyl-2-Methylpenam-3-Carboxylate, 1, (R=φOCH₂, R¹=CH₃, R²=H) from Sym-(Methyl 3-Phenoxyacetamidoazetidinone-1-Isopropyl Acetate)-4-Disulfide, 4 (R=φOCH₂, R¹=CH₃, R²=H)

A solution of sym-(methyl 3-phenoxyacetamidoazetidinone-1-isopropenyl acetate)-4-disulfide in methylene chloride was iodinated in the same manner as described in Example 7 to give the 2-iodomethylpenam, 1.

EXAMPLE 10

Methyl 6-Phenoxyacetamido-2-Iodomethyl-2-Methylpenam-3-Carboxylate, 1 (R=φOCH₂, R¹=CH₃, R²=H) from Methyl 2-Oxo-3-(2-Phenoxyacetamido)-4-(Benzothiazol-2-yl)Dithio-α-Isopropenylazetidin-1-Acetate, 5, (R = φOCH₂, R¹ = CH₃, R² = H, R⁵ = 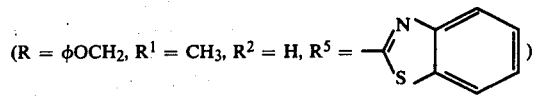 )

A solution of iodine (1 at. eq.) in methylene chloride was added in one lot to a stirred ice-cold solution of methyl 2-oxo-3-(2-phenoxyacetamido)-4-(benzothiazol-2-yl)dithio-α-isopropenylazetidin-1-acetate in methylene chloride and the mixture stirred at 0° for 30 mins. The reaction mixture was then washed with aqueous sodium thiosulfate, then water and dried over magnesium sulfate. Concentration of the filtrate gave a white foam which consisted of about 30% of the 2-iodomethylpenam and about 70% of the starting material 5.

In a similar manner starting from benzhydryl 2-oxo-3-(2-phenoxyacetamido)-4-(benzothiazol-2-yl)dithio-α-isopropenylazetidin-1-acetate, trichloro ethyl 2-oxo-3-(2-phenoxyacetamido)-4-(benzothiazol-2-yl)dithio-α-isopropenylazetidin-1-acetate, p-nitrobenzyl 2-oxo-3-(2-phenoxyacetamido)-4-(benzothiazol-2-yl)dithia-α-isopropenylazetidin-1-acetate, methoxymethyl 2-oxo-3-(2-phenoxyacetamido)-4-(benzothiazol-2-yl)dithio-α-isopropenylazetidin-1-acetate, trimethylsilyl 2-oxo-3-(2-phenoxyacetamido)-4-(benzothiazol-2-yl)dithio-α-isopropenylazetidin-1-acetate, benzhydryl 2-oxo-3-(2-phenylacetamido)-4-(benzothiazol-2-yl)dithio-α-isopropenyl-1-acetate, methoxymethyl 2-oxo-3-(2-phenylacetamido)-4-(benzothiazol-2-yl)dithio-α-isopropenylazetiin-1-acetate, trimethylsilyl 2-oxo-3-(2-phenylacetamido)-4-(benzothiazol-2-yl)dithio-α-isopropenylazetidin-1-acetate, t-butyl 2-oxo-3-(2-phenylacetamido)-4-(benzothiazol-2-yl)dithio-α-isopropenylazetidin-1-acetate, benzhydryl 2-oxo-3-(N-carbobenzyloxy-α-aminophenylacetamido-4-(benzothiazol-2-yl)dithio-α-isopropenylazetidin-1-acetate, and methoxymethyl 2-oxo-3-(N-methoxymethoxycarbonyl-α-aminophenylacetamido)-4-(benzothiazol-2-yl)dithio-α-isopropenylazetidin-1-acetate, the following 2-iodomethylpenams can be prepared:
  benzhydryl 6-phenoxyacetamido-2-iodomethyl-2-methylpenam-3-carboxylate, trichloroethyl 6-phenoxyacetamido-2-iodomethyl-2-methylpenam-3-carboxylate, p-nitrobenzyl 6-phenoxyacetamido-2-iodomethyl-2-methylpenam-3-carboxylate, methoxymethyl 6-phenoxyacetamido-2-iodomethyl-2-methylpenam-3-carboxylate, 6-phenoxyacetamido-2-iodomethyl-2-methylpenam-3-carboxylic acid, benzhydryl 6-phenylacetamido-2-iodomethyl-2-methylpenam-3-carboxylate, methoxymethyl 6-phenylacetamido-2-iodomethyl-2-methylpenam-3-carboxylate, 6-phenylacetamido-2-iodomethyl-2-methylpenams-3-carboxylic acid, t-butyl 6-phenylacetamido-2-iodomethyl-2-methylpenam-3-carboxylate, benzhydryl 6-N-carbobenzyloxy-α-aminophenylacetamido-2-iodomethyl-2-methylpenam-3-carboxylate, and methoxymethyl 6-N-methoxymethoxycarbonyl-α-aminophenylacetamido-2-iodomethyl-2-methylpenam-3-carboxylate.

EXAMPLE 11

Benzhydryl 7-Phenoxyacetamido-3-Iodo-3-Methylcepham-4-Carboxylate, 6 (R=φOCH$_2$, R$^1$=CHφ$_2$, R$^2$=H) from Benzhydryl 6-Phenoxyacetamido-2-Iodomethyl-2-Methylpenam-3-Carboxylate, 1, R=φOCH$_2$, R$^1$=CHφ$_2$, R$^2$=H).

A methylene chloride solution of a sample containing 71.5% of the 2-iodomethylpenam, 1, and 28.5% of the 3-iodocepham, 6, was left at room temperature for one week. Analysis of the mixture showed the presence of about 90% of the 3-iodocepham, 6.

EXAMPLE 12

Benzhydryl 7-Phenoxyacetamido-3-Methylceph-3-em-4-Carboxylate from Benzhydryl 7-Phenoxyacetamido-3-Iodo-3-Methylcepham-4-Carboxylate, 6 (R=φOCH$_2$, R$^1$=CHφ$_2$, R$^2$=H)

Benzhydryl 7-phenoxyacetamido-3-iodo-3-methylcepham-4-carboxylate, 6 (309 mg., 0.48 mmoles) was dissolved in ice-cold deuteropyridine (1 ml) and the progress of the reaction followed by nmr spectroscopy. The reaction was complete after 1 hr at ambient temperature. The pyridine was removed under vacuum, the residue dissolved in methylene chloride and the solution washed with dilute (1 normal) hydrochloric acid and water. The dried organic layer on concentration gave 0.25 g. of a yellow foam, whose nmr and thin layer chromatogram showed that it was the ceph-3-em. Purification by column chromatography on Silica gave 0.2 g. of the ceph-3-em. The nmr (CDCl$_3$) spectrum, δ2.15 (s, 3H, C$_3$—CH$_3$), 3.3 (ABq, 2H, C$_2$-CH$_2$), 4.65 (s, 2H, —OCH$_2$), 5.05 (d, 1H, C$_6$-H), 5.93 (q, 1H, C$_7$—H), 7.0 to 7.65 (m, 17H, Aryl H's, CHφ$_2$ and NH) is characteristic.

EXAMPLE 13

Benzhydryl 6-Phenoxyacetamido-2-Iodomethyl-2-Methylpenam Sulfoxide-3-Carboxylate, 10 (R=φOCH$_2$, R$^1$=CHφ$_2$, R$^2$=H) and Benzhydryl 7-Phenoxyacetamido-3-Iodo-3-Methylcepham Sulfoxide-4-Carboxylate Benzhydryl 3-phenoxymethyl-4-thia-2,6-diazabicyclo[3.2.0]hept-2-ene-7-one-6-isopropenylacetate, 2 (R=φOCH$_2$, R$^1$=CH$_3$, R$^2$=H; 5 g., 10 mmoles) was added to a stirred solution of iodine (4.23 g., 16.6 mmoles) in methylene chloride (80 ml). To the stirred reaction mixture, water (80 ml) saturated with air was added and the mixture stirred vigorously for 1.5 hrs (an aliquot worked up after 1 hr showed no starting material in its nmr spectrum). The mixture was washed with aqueous sodium thiosulfate, then water, and dried. The filtered solution was reacted with m-chloroperbenzoic acid (85%, 2.4 g., 12 mmoles) at 0° to 5° C. After 15 mins at this temperature the reaction mixture was stirred 30 mins at ambient temperature, then washed with saturated sodium bicarbonate, then water and dried (magnesium sulfate and decolorising charcoal). Concentration of the filtrate gave a yellow green foam weighing 6.3 g. Column chromatography on Silica gel using methylene chloride - ether gradient elution chromatography gave 1.84 g., of the pure benzhydryl 6-phenoxyacetamido-2-iodomethyl-2-methylpenam sulfoxide-3-carboxylate, 10, and 1.3 g., of the pure 3-iodocepham sulfoxide. The nmr spectra of these two compounds were characteristic.

The nmr (CDCl$_3$) spectrum of the 2-iodomethylpenam sulfoxide, δ1.08 (s, 3H, C$_2$—CH$_3$), 3.88 (ABq, 2H, C$_2$—CH$_2$I), 4.62 (s, 2H, OCH$_2$), 5.0 (ds, 2H, C$_3$—H and C$_5$—H), 6.20 (q, 1H, C$_6$—H), b 7.0 to 7.7 (m, 16H, aryl H's and CHφ$_2$), 8.4 (d, 1H, NH), and the 3-iodocepham sulfoxide, δ1.7 (s, 3H, C$_3$—CH$_3$), 3.32 (ABq, 2H, C$_2$—CH$_3$), 4.4 (s, 2H, OCH$_2$), 4.72 (s, 1H, C$_4$—H), 4.83 (d, 1H, C$_6$—H), 5.6 (q, 1H, C$_7$—H), 6.7 to 7.5 (m, 17H, aryl H's, CHφ$_2$ and NH) are different from each other and sufficient to characterise the compounds.

EXAMPLE 14

Benzhydryl 6-Phenoxyacetamido-2,3-Methylenepenam-3-Carboxylate, 9 (R=φOCH$_2$, R$^1$=CHφ$_2$, R$^2$=H) from Benzhydryl 6-Phenoxyacetamido-2-Iodomethyl-2-Methylpenam-3-Carboxylate, 1 (R=φOCH$_2$, R$^1$=CHφ$_2$, R$^2$=H)

A mixture containing about 60% benzhydryl 6-phenoxyacetamido-2-iodomethyl-2-methylpenam-3-carboxylate, 1 and about 40% of the 3-iodocepham was dissolved in methylene chloride and cooled to −30° C. 1,5-Diazobicyclo[5.4.0]undec-5-ene (DBU, 1 equivalent) was added and the mixture stirred at −30° C. for 2 hrs. The reaction mixture was washed with dil. (1 normal) hydrochloric acid and water, then dried (magnesium sulfate) and concentrated to a yellow wax. The nmr spectrum of the product showed the presence of about 30% of the 2,3-methylenepenamd, 9. This compound was purified by silica column chromatography as a pale yellow foam; nmr (CDCl$_3$) δ1.55 (s, 3H, C$_2$-CH$_3$), 2.20 (s, 2H, C$_{2,3}$-CH$_2$), 4.46 (s, 2H, CH$_2$O), 5.58 (q, 1H, C$_6$-H), 6.18 (d, 1H, C$_5$-H), and 6.78 to 7.58 (m, 16H, aryl H and CHφ$_2$).

Essentially the same results were obtained by using tetrahydrofuran (3 hrs at −30° C.) or dimethyl formamide (1 hr at −30° C.) as solvents. The yields of the 2,3-methylenepenam has not been optimised.

EXAMPLE 15

Benzhydryl 6-Phenoxyacetamido-2,3-Methylenepenam Sulfoxide-3-Carboxylate, 11 (R=φOCH$_2$, R$^1$=CHφ$_2$, R$^2$=H) from Benzhydryl 6-Phenoxyacetamido-2-Iodomethyl-2-Methylpenam Sulfoxide-3-Carboxylate, 10 (R=φOCH$_2$, R$^1$=CHφ$_2$, R$^2$=H)

Benzhydryl 6-phenoxyacetamido-2-iodomethyl-2-methylpenam sulfoxide-3-carboxylate, 10, when treated in DBU in DMF at −30° for 1 hr gave the desired benzhydryl 6-phenoxyacetamido-2,3-methylenepenam sulfoxide-3-carboxylate 11.

The same compound 11, was obtained by oxidising benzhydryl 6-phenoxyacetamido-2,3-methylenepenam-3-carboxylate, 9, using compounds such as m-chloroperbenzoic acid or peracetic acid.

I claim:

1. A process for preparing a 2-iodomethylpenam of the formula 1.

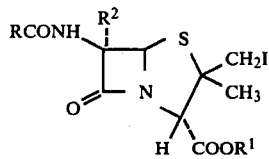

in which RCO is a conventional penicillin acyl moiety, $R^1$ is a conventional penicillin protecting group and $R^2$ is hydrogen or methoxy, which comprises treating an azetidinone derivative selected from those of formulae 2 and 3

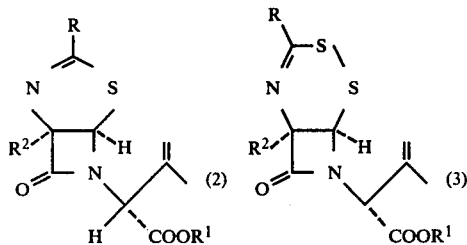

in which R, $R^1$ and $R^2$ are as defined above, with iodine dissolved in a solvent, in the presence of a catalyst selected from the group consisting of air, oxygen and ferric chloride, and in the presence of moisture, at 0°–25° C., for a period of time of from five minutes to six hours, and isolating said 2-iodomethylpenam of formula 1.

2. The process of claim 1, wherein R stands for hydrogen, $C_{1-4}$ alkyl, cyanomethyl, thienylmethyl, furylmethyl, tetrazolylmethyl, phenylmethyl, phenoxymethyl, phenoxyisopropyl, $R^3$-O, $R^3$S- and $R^3R^4$N- wherein $R^3$ is lower alkyl, phenyl, phenylloweralkyl or trichloroethyl; $R^4$ is hydrogen or has the same value as $R^3$; α-hydroxybenzyl, α-aminobenzyl or benzyl-α-carboxylic acid wherein the α-hydroxy, α-amino or α-carboxylic acid moieties may be protected by a conventional penicillin, easily removable protecting group, and $R^1$ is lower alkyl, 2,2,2-trichloroethyl, benzyl, p-nitrophenyl, p-methoxybenzyl, benzhydryl, fluorenyl, phenacyl, methoxymethyl, phenoxymethyl, benzyloxymentyl or trimethylsilyl.

3. The process of claim 1 wherein the azetidinone derivative treated has formula (2).

4. The process of claim 1 wherein the azetidinone derivative treated has formula (3).

5. The process of claim 1 wherein the catalyst is air.
,31

6. The process of claim 1, wherein benzhydryl 3-phenoxymethyl-4-thia-2,6-diazabicyclo[3.2.0]hept-2-ene-7-one- 6-isopropenyl acetate is reacted with iodine in the presence of air and moisture to form the benzhydryl 6-phenoxyacetamido-2-iodomethyl-2-methylpenam-3-carboxylate.

7. The process of claim 1, wherein benzhydryl 3-phenoxymethyl-4,5-dithia-2,7-diazabicyclo[4.2.0]oct-2-ene-8-one-7-isopropenyl acetate is reacted with iodine in the presence of air and moisture to form the benzhydryl 6-phenoxyacetamido-2-iodomethyl-2-methylpenam-3-carboxylate.

* * * * *